(12) United States Patent
Mullen

(10) Patent No.: US 6,749,861 B2
(45) Date of Patent: Jun. 15, 2004

(54) FRAGRANCE-CONTAINING INSECT REPELLANT COMPOSITIONS

(75) Inventor: Patricia A. Mullen, Babylon, NY (US)

(73) Assignee: Lenco Laboratories, LLC, Lindenhurst, NY (US)

(*) Notice: Subject to any disclaimer, the term of this patent is extended or adjusted under 35 U.S.C. 154(b) by 98 days.

(21) Appl. No.: 10/028,597

(22) Filed: Dec. 20, 2001

(65) Prior Publication Data

US 2003/0017178 A1 Jan. 23, 2003

Related U.S. Application Data

(63) Continuation-in-part of application No. 09/896,972, filed on Jun. 29, 2001, now Pat. No. 6,346,297.

(51) Int. Cl.$^7$ .............................. A01N 25/00; A61L 9/00; A61L 9/01; B05D 3/02; A61K 9/00; A61K 7/46
(52) U.S. Cl. ..................... 424/405; 424/76.1; 424/76.8; 424/400; 427/385.5; 512/1

(58) Field of Search .................................. 424/405, 400, 424/76.1, 76.8; 512/1; 427/385.5

(56) References Cited

U.S. PATENT DOCUMENTS

| | | | | | |
|---|---|---|---|---|---|
| 5,102,662 | A | * | 4/1992 | Gallagher | 424/405 |
| 5,776,478 | A | * | 7/1998 | Jain | 424/405 |
| 6,346,297 | B2 | * | 2/2002 | Mullen | 427/385.5 |

* cited by examiner

*Primary Examiner*—Shelley A. Dodson
(74) *Attorney, Agent, or Firm*—Kramer, Levin, Naftalis & Frankel LLP

(57) ABSTRACT

An insect composition comprising at least one fragrance capable of repelling insects and at least one non-fragrance insect repellant which is soluble in the fragance. In preferred embodiments the composition also includes an absorption substrate carrier. These compositions provide effective contact and area repellency while maintaining a pleasant aroma.

26 Claims, 2 Drawing Sheets

FRAGRANCE-CONTAINING INSECT REPELLANT COMPOSITIONS

RELATED APPLICATION

This application is a continuation-in-part of U.S. application Ser. No. 09/896,972 filed Jun. 29, 2001 now U.S. Pat. No. 6,346,297, which application is hereby incorporated by reference in its entirety.

BACKGROUND OF THE INVENTION

Paper has been used as a substrate for fragrances. Many examples of paper-based fresheners may be found on the market. However, the combination of fragrance(s), paper, and adhesives has not been feasible because fragrances are good solvents. When a fragrance is absorbed into the paper substrate, any adhesive bond with the paper substrate is destroyed. Either the adhesive is dissolved or it is softened to the point where the adhesion is lost.

Also, fragrance-impregnated paper exhibits problems of maintaining fragrance quality and controlled release. Therefore, there is a need for a fragrance-containing composition which can be coated on the surface of the paper to exhibit both controlled release of the fragrance and controlled absorption of the fragrance into the paper, and which will not penetrate to the back of the paper.

Certain fragrances exhibit the ability to repel insects and other pests. These fragrances can be impregnated on paper to form insect repellants. The efficacy of such insect repellants can be increased if the fragrance-containing insect repellants were used in combination with non-fragrance insect repellants. Thus, there is a need for a composition containing fragrance-containing insect repellant compositions with non-fragrance insect repellants. There is a further need for effective fragrance-containing insect repellant compositions which combine the benefits of an area repellent with the benefits of a contact repellant.

SUMMARY OF THE INVENTION

A fragrance-containing coating composition for paper substrates consists essentially of (a) a polyvinyl chloride plastisol (PVC plastisol) and (b) one or more fragrances. PVC plastisol is a dispersion which typically contains polymer and a plasticizer(s). The paper substrate can be a non-calendered, non-coated porous paper, a coated, non-calendered paper, or a calendered, optionally coated paper. When the paper is calendered and/or coated the PVC plastisol can further contain an adhesion promoter.

The fragrance can be of many types; e.g., a fruit fragrance, a citrus fragrance, a floral fragrance, a woody fragrance, a leather fragrance, an oriental fragrance, a mint fragrance, and/or a food fragrance.

The coating composition may further consist essentially of a diluent as well as a component which has a synergistic effect when combined with the fragrance(s), e.g., phthalates.

The coating composition is applied at room temperature to at least one side of the paper substrate as a film. The coated paper substrate is rapidly heated at a temperature (e.g., 320° F.) and for a time (e.g., 15–20 seconds) sufficient to fuse the film to a clear coating and adhere it to the paper substrate without causing significant volatilization of the fragrance(s). The heated paper substrate is then cooled and stored until use in a barrier material such as polyethylene terephthate-coated polyethylene, or an aluminum-coated polyethylene. One side of the paper substrate may be coated with a pressure sensitive adhesive prior to coating when the preferred PVC plastisol is used.

The advantages of the above coating composition include good adhesion to the paper substrate, rapid drying under conditions which do not adversely affect the fragrance(s), clarity on drying which is important when graphics are present on the paper, and, compatibility with all paper grades. In addition, the plastisol has a low odor, has a low or no solvent content, is compatible with a wide range of fragrances, and will accept reasonably high levels of fragrance(s) and still retain the fragrance's notes.

This new plastic coating maintains fragrance quality, coating clarity, and paper adhesion and is useful for coating all grades of paper.

An insect repellant composition comprises at least one fragrance capable of repelling insects and at least one non-fragrance insect repellant. A preferred composition comprises a combination of one or more high vapor pressure aroma chemicals or fragrance materials having insect repellant properties and one or more low vapor pressure "non-fragrance" insect repellants, such as N,N-diethyl-m-toluamide (DEET). The low vapor pressure chemical dissolves in the high vapor pressure fragrance, allowing the low vapor pressure chemical to exhibit both contact and area repellency. Such compositions also can include an absorption substrate carrier. These compositions provide an effective contact and area repellant while providing a pleasant aroma.

BRIEF DESCRIPTION OF THE FIGURE

The following figure is illustrative of embodiments of the invention and is not meant to limit the scope of the invention as encompassed by the claims.

DESCRIPTION OF THE PREFERRED EMBODIMENTS

Figure 1:
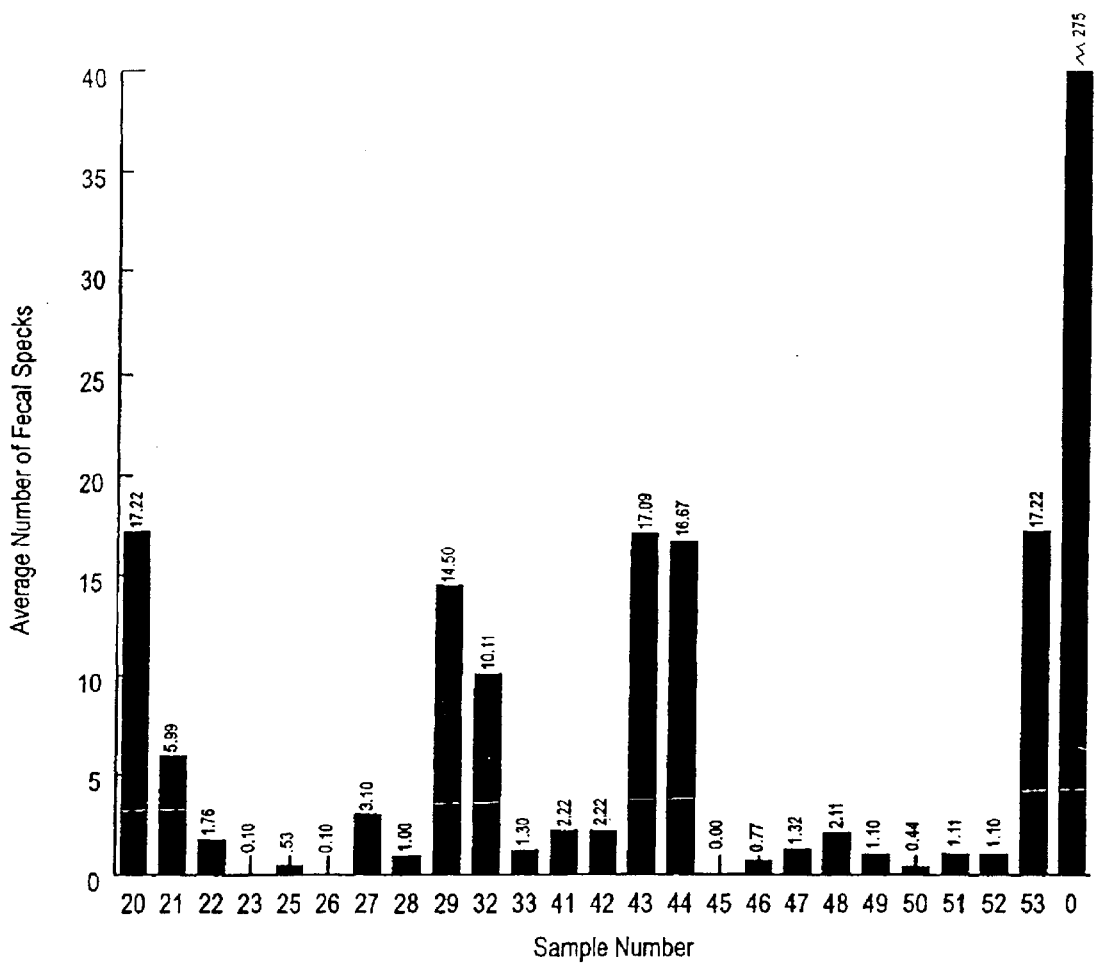
FIG. 1 is a bar graph showing the average number of fecal specks present on fragrance blotters exposed to *Musca domestica* (house flies)

The present invention provides fragrance-containing coating compositions for paper substrates and also provides fragrance-containing insect repellant compositions. Preferred embodiments of each are described below.

Fragrance-Containing Coating Compositions For Paper Substrates

As used herein, the term "porous papers" refers to papers such as reply cards which are not calendered or coated.

As used herein, the term "papers with a vellum finish" refers to papers which are not calendered for smoothness. These papers have fibers protruding from the surface and are not coated.

As used herein, the term "coated paper substrates" refers to papers which are calendered for smoothness as well as papers which are calendered and clay-coated. Such papers may be matte finish, dull finish, regular finish, and cast-coated finish types. Papers with a matte finish are coated with an aqueous clay formulation consisting primarily of clay and optionally titanium dioxide. Papers with a dull finish are clay coated and calendered to provide a slight sheen on the surface. Papers with a regular finish have a heavy clay coating which is buffed and calendered for gloss. Papers with a cast-coated finish have the regular finish discussed above and are provided with additional calendering and/or coating to provide a mirror-like finish.

As used herein, the word "fragrance" refers to a mixture which provides a liquid with a pleasing odor. The fragrance may include two or more components and optionally a fixative or synergistic component which increases the fragrance's odor and permits the use of smaller amounts of the fragrance component(s). The fragrance, for example, can also be a volatile and fragrant aroma chemical, including, but not limited to, eucalyptus, lanolin or geraniol.

As used herein the word "plastisol" refers to thermoplastics which require heat for fusion. Plastisols are dispersions which have a "milky" appearance. Prior to fusion, the plastisol film coated onto the substrate is "cloudy" or "milky." After fusion the plastisol film is completely clear. A "cloudy" or "milky" appearance indicates incomplete fusion.

Polyvinyl chloride (PVC) plastisols suitable for use herein contain polymers, plasticizers, and, when the paper is a smooth and/or coated, non-porous paper, an adhesion promoter or enhancer. The preferred polyvinyl chloride plastisol for smooth non-porous papers is a white or colored liquid which is available from Rutland Plastics Technologies, Inc. (Pineville, N.C.) under the trade name NG0026 Thermo-O-Line. It has a gel point of 165° F. and a flash point of greater than 400° F. It should be stored at 65–97° F. to avoid "gelling." Another preferred polyvinyl chloride plastisol includes NG0165, also available from Rultland Plastic Technologies, Inc. Pigment concentrates may be added to this plastisol in amounts of up to about 10–15% by weight if a tinted plastisol is desired.

Typically the coating thicknesses range from about 2–50 mils, preferably about 2–20 mils.

The maximum amount of fragrance which can be used is that amount which is soluble in the PVC plastisol and which does not destroy the film-forming properties. The minimum amount of fragrance is that amount which is required to provide a fragrance strong enough to last for the desired period of time. The amount of fragrance added to the PVC plastisol coating composition is 1% to about 20%, preferably about 6% to about 15%, most preferably about 13%, by weight, which amount will depend upon the particular fragrance(s) selected.

Fragrances in all odor categories are useful herein, for example, fruit fragrances such as strawberry, raspberry, peach, cherry, apple and pear; citrus fragrances such as orange, lemon, grapefruit, and lime; floral fragrances such as rose, hyacinth, lilac, lily-of-the-valley, calyx, osmanthus, orange blossom, apple blossom, rose, and freesia; woody fragrances such as cedarwood, sandalwood, oak, and pines; leather fragrances, i.e., dominant notes from the quinoline family; oriental fragrances such as musk, vanillin, laubdanum, and oak moss notes; aldehydic notes; mint fragrances such as spearmint and peppermint; and food fragrances such as vanilla, chocolate, chocolate mint, pizza, popcorn, barbecued meats (beef and chicken).

In many cases there is more than one way of achieving a particular fragrance type. A typical fragrance composition is composed of top-, middle-, and bottom-notes. The top-note(s) are the most volatile. The bottom-notes are the least volatile and are the residual on the surface which gives the fragrance a lasting quality. However, all of the notes contribute to the perception of the fragrance. For the type of use described herein, heat-stable fragrances are preferred.

Because the coating after fusion is glossy and transparent, it is particularly useful on printed paper substrates because the graphics can still be easily seen.

Preferably, a single coating having a thickness of about 2–50 mils., preferably about 2–20 mils., is applied at room temperature to one surface of the paper substrate. The thickness of the coating should not be thicker than that which can be fused during heating. If desired, more than one coating can be applied provided the coating is allowed to dry thoroughly between coatings. If desired, both sides of the paper substrate can be coated, in which case less fragrance will be needed to obtain the desired effect.

The coating is set by quickly heating the coated paper substrate. For example, the coated paper substrate is placed on a movable belt and quickly moved through a heating tunnel where the peak temperature is sufficient to fuse the film. Typically the peak temperature is about 320° F.; the exposure time to this temperature depends upon the thickness of the film. If the film is about two to about four mils in thickness, the fusion time will be about thirty seconds. The peak temperature and residence time in the tunnel should be sufficient to provide a clear, not "milky," and non-tacky coating.

After cooling the fused coated paper substrate can be cut into any desired shape. If desired, a tacky adhesive can be applied to the uncoated side of the paper substrate before or after the coating so that the coated product can be adhered to a person's clothing or other object. If not used immediately, the fragrance-coated substrate should be packaged so the fragrance does not prematurely evaporate from the coating. Evaporation is prevented by covering the coated paper substrate with a barrier material such as polyethylene terephthalate-coated polyethylene or aluminum-coated polyethylene, and the like.

Fragrance-Containing Insect Repellant Compositions

Fragrance-containing insect repellant compositions may include those which can be used to coat paper substrates when combined with, for example, a PVC plastisol, as described above. Fragrance-containing insect repellant compositions also may include those which comprise at least one fragrance capable of repelling insects and at least one non-fragrance insect repellant such as N, N-diethyl-m-toluamide (DEET). Such compositions also may include an absorption substrate carrier.

For either type of composition (i.e., coatings for paper substrates, or combination fragrance/non-fragrance insect repellants) a preferred fragrance includes insect repellants which have been formulated to contain a mixture of volatile natural and/or synthetic components called fragrances because of their volatility and olfactory properties. Insect repellant fragrances may be constructed of top-, middle-, and bottom-notes. In preferred embodiments, the fragrance is formulated to contain more than one insect repellant. Insects which can be repelled include, but are not limited to house flies, mosquitoes, yellow jackets, and ants.

Natural ingredients which act as insect repellants include, for example, salicylates, benzoates, lemon and orange oils, citronella oil, geraniol, terpineol, garlic oil, grapefruit oil, mints, southernwood, and tea tree oil.

When the fragrance is used in a coating composition the insect repellant should be long-lasting. Whether a fragrance remains long-lasting is influenced by several factors which include the PVC plastisol carrier being used. In coating compositions, the insect repellents listed above are used in amounts ranging from 0.3% to greater than 20% by weight of the composition in a finished formula. The choice of an amount depends upon the repellency properties sought and the odor properties desired. For example, in the range of 0.3% to 1% one may use geraniol, lavender oil, camphor oil, and/or cinnamon oil; in the range of 1% to 10% one may use various acetates, citronella oil, lemon oil, orange oils, and terpineols; and in the range above 10% one may use lemon or orange oils and benzoates. Diluents such as glycols, alcohols, and/or phthalates, may also be added.

An insect repellant composition also may comprise at least one fragrance capable of repelling insects and at least one non-fragrance insect repellant. An especially preferred composition comprises a combination of one or more high vapor pressure insect repellant fragrances and one or more low vapor pressure non-fragrance insect repellants. As used herein, a low vapor pressure insect repellants such as DEET is considered to be a non-fragrance. Also, the fragrances herein, and any aroma chemicals used to create the fragrances, are considered to be high vapor pressure substances. Any other aroma chemical with insect repellant properties also is a high vapor pressure substance in accordance with the present invention.

Examples of high vapor pressure fragrances include, but are not limited to salicylates, benzoates, lemon and orange oils, citronella oil, geraniol, terpineol, garlic oil, grapefruit oil, mints, southernwood, and tea tree oil. Especially preferred fragrances that have citrus and/or pine notes.

Examples of low vapor pressure non-fragrance insect repellants include, but are not limited to, DEET, dimethyl phthalate (DMP), dibutyl phthalate (DBP), and pyrethrin insecticides including N-octyl bicycloheptane dicarboximide, such as MGK-264. Any other low vapor pressure non-fragrance insect repellants that are completely soluble with the high vapor pressure fragrances would be suitable for the present invention. The concentration range of the low vapor pressure non-fragrance insect repellant can range from about 1% to about 80%, e.g., from about 1% to about 50%, e.g., from about 1% to about 10%, e.g., from about 1% to about 5%.

In especially preferred embodiments the insect repellant fragrance and non fragrance compositions also comprise an absorption substrate carrier. Absorption substrate carriers may include any material which can absorb the repellant composition. The carrier may include solid substrates such as paper, plastics, fabric, clay, or porous polyethelene, for example. Carriers also may include a liquid in a film pouch, wax, gels, PVC plastisols, polypropylene or consumer products such as wicking candles or other passive air fresheners.

In other embodiments, the combination of the insect repellant fragrances and non-fragrance compositions can be incorporated into other formulation systems. Formulation systems may include, emulsions such as creams and lotions, solutions, suspensions, and gels. The insect repellant fragrance and non-fragrance compositions also can be added to plastics.

When a PVC plastisol is used as an absorption substrate carrier, the insect repellant composition may be applied as a coating for paper substrates as described below.

As shown in FIG. 1 and in Example 3, the combinations of high vapor pressure fragrances and low vapor pressure insect repellants on a paper blotter absorption substrate carrier exhibit a much greater repellency effect than the insect repellant fragrance alone. Further, the addition of an insect repellant fragrance to a low vapor pressure insect repellant does not diminish the effectiveness of the low vapor pressure insect repellant as a contact repellant. Thus, one embodiment of the present invention provides a composition which is an effective contact repellant and also has a pleasant aroma.

Figure 2:
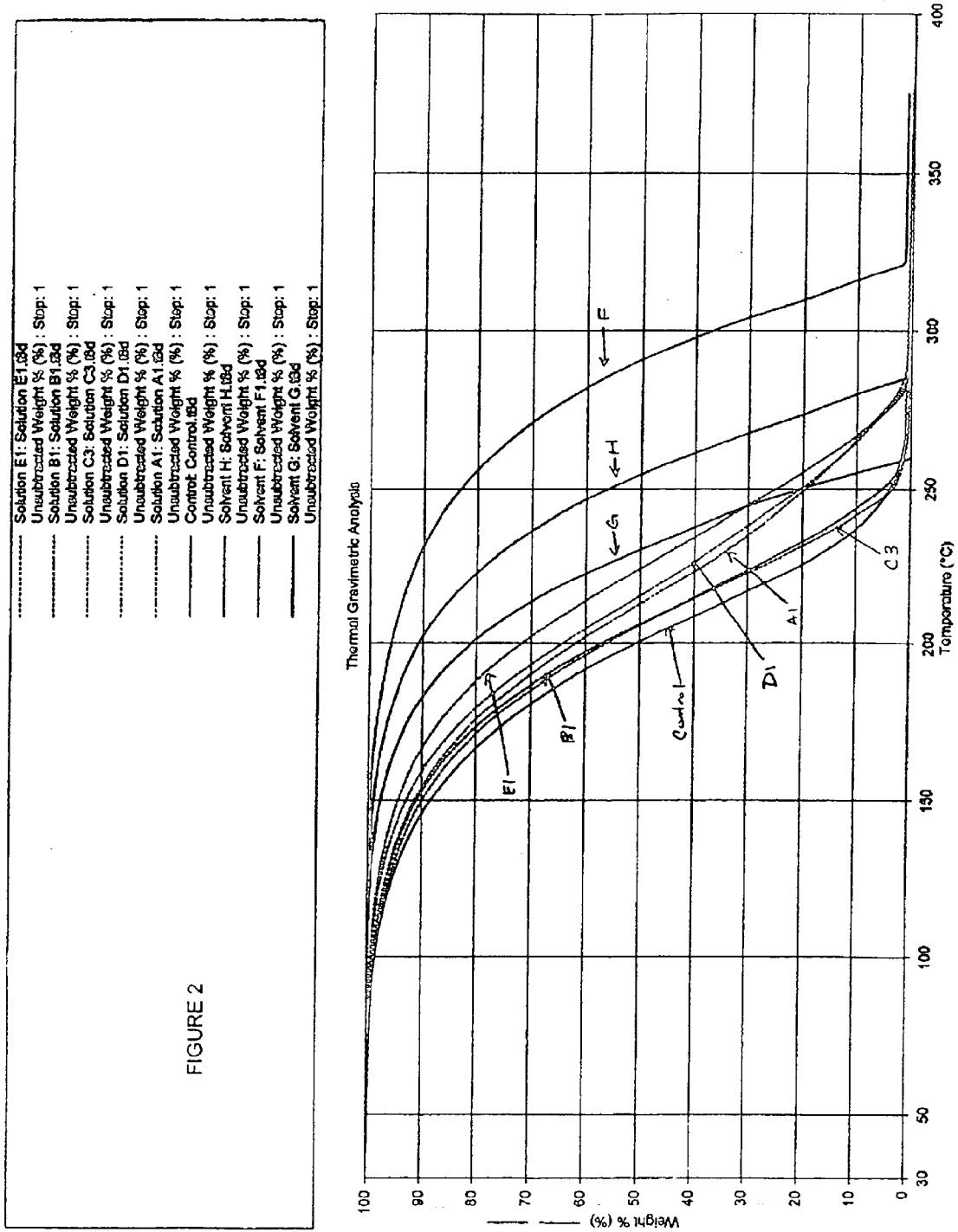
FIG. 2 depicts thermograms obtained from thermogravimetric analysis (TGA) of samples of low vapor pressure insect repellants in combination with a high vapor pressure insect repellant fragrance.

Low vapor pressure insect repellants, such as DEET, do not evaporate to a significant extent and, therefore, are considered contact repellants. Contact repellants deter insects from landing or otherwise contacting the surface covered by the contact repellant. Insect repellant fragrances are considered area repellants, since evaporation of the fragrances establishes an area of protection in which insects are deterred from entering. The present invention provides for compositions having the benefits of low vapor pressure contact repellants and the benefits of high vapor pressure area repellant fragrances. Without being bound by a particular theory, it is believed that low vapor pressure insect repellant chemicals completely dissolve in high vapor pressure insect repellant fragrances, such as those described above. In other words, the low vapor pressure insect repellant chemicals and the high vapor pressure insect repellant fragrances are entirely soluble with each other. As shown in FIGS. 1 and 2 and Example 4, thermogravimetric analysis (TGA) was performed on various samples containing low vapor pressure insect repellant chemicals in combination with high vapor pressure insect repellant fragrances. These samples were analyzed by thermogravimatric analysis which is a test for measuring the changes in the weight of a sample as a function of temperature. Each of the thermograms shown in FIG. 2 are smooth thus showing that the low vapor pressure insect repellant chemicals are indeed completely dissolved in the high vapor pressure insect repellant fragrances.

Thus, one embodiment of the present invention allows a low vapor pressure insect repellant, such as DEET to exhibit its effects as an area repellant and not just as a contact repellant.

The fragrance and non fragrance repellants are formulated by adding a high vapor pressure fragrance to a vessel and subsequently adding the low vapor pressure insect repellant. The ingredients are stirred or mixed until a clear solution is obtained. Any suitable means, such as stir bars or mixers, can be used for the agitation.

The following examples illustrate various aspects of the present invention and are not meant to be construed to limit the claims in any manner whatsoever.

EXAMPLE 1

This example describes the preparation of a fragrance which is a natural insect repellent and its inclusion in the polyvinyl chloride (PVC) plastisol which is sold under the trade name NG0026 Thermo-O-Line by Rutland Plastic Technologies.

The fragrance was obtained by mixing the following ingredients:

| Ingredient | Wt. % |
|---|---|
| Eucalyptus Oil | 0.3 |
| Cedarwood Oil | 0.7 |
| Citronella Oil | 10.0 |
| Pine Oil | 25.0 |
| Camphor Oil | 1.0 |
| Linalool | 1.0 |
| Linalyl Acetate | 1.0 |
| Lemon Oils | 10.0 |
| Phenylethyl Alcohol | 7.0 |
| Terpineol | 3.0 |
| Galbanum Oil | 1.0 |
| Benzyl Acetate | 15.0 |
| Turpentine | 2.0 |
| Patchouli | 5.0 |
| Benzyl Alcohol | 2.0 |
| Isoamyl Salicylate | 1.0 |
| Isopropyl Myristate | 2.0 |
| Isopropyl Palmitate | 4.0 |
| Dipropylene Glycol | 9.0 |
| | 100.0% |

A total of 10% (w/w) of the above fragrance was included in the PVC plastisol. One gallon was sufficient to coat 325 square feet of the paper.

The coating thickness was four mils. For testing one square inch portions of the paper were coated and the coating was fused at 320° F. for fifteen seconds, cooled, and placed in a barrier bag. The coating parameters were chosen to provide a product life of eight hours. The aroma was evaluated after storage in the barrier for five days. After storage in the barrier bags for five days, the coated paper samples were taken out and placed on a flat surface. The odor of the samples was evaluated over a period of twenty-four hours at which time the test was discontinued.

All of the papers listed below are calendered papers. Some are coated and some are embossed and uncoated. All are 65–80 lbs. stock.

The results are summarized below in Table 1.

TABLE 1

Organoleptic Evaluation

| Textured Paper Substrate | |
|---|---|
| Ultrafelt Text (acid-, alum-, and rosin-free) | Good initial fragrance strength and good fragrance retention |
| Pageantry Cover Canvas (uncoated) | Good initial fragrance strength and good fragrance retention |
| Champion Cordwain Cover (uncoated) | Good initial fragrance strength and good fragrance retention |
| Champion Linen Cover | Good initial fragrance strength and good fragrance retention |
| Champion Felt Cover (alkaline sheets) | |
| Irish Linen Cover (acid-, alum-, and rosin-free) | Fragrance perceived was missing top notes initially and fragrance faded rapidly |
| George A. Whiting (acid-free, 100% recycled) | Fragrance perceived was missing top notes initially and fragrance faded rapidly |
| Smooth Paper Substrates | |
| Augusta Bristol (0.007) | Good initial strength and good retention |
| Augusta Bristol (0.008) | Good initial strength and good retention |
| Augusta Bristol (0.009) | Good initial strength and good retention |
| Hammermill Cover | Fragrance perceived was missing top notes initially and fragrance faded with time |
| Weyerhauser Husby (Smooth Scoff) | |
| Appleton Crystin Cover (coated paper) | Fragrance perceived was missing top notes initially and fragrance faded rapidly |
| Pageantry Cover Vellum (uncoated) | Fragrance perceived was missing top notes initially and fragrance faded rapidly |

EXAMPLE 2

The fragrance described in Example 1 is added at 10% (w/w%) to an opaque, high viscosity, white PVC plastisol, which is sold under the trade name NH-LB LOW-BLEED by Rutland Plastic Technologies, which has a gel point of 165° F. and a fusion temperature 320° F. The fragrance containing PVC plastisol is coated onto vellum, reply cards, or other uncalendered papers using an amount sufficient to provide a coating having a coating thickness of about 2–20 mils. The coating is fused at 320° F. for about fifteen seconds, cooled, and stored in barrier bags.

EXAMPLE 3

This example demonstrates the insect repellant effects of various fragrances and chemicals, alone and in combination.
Materials And Methods Twenty-five liquid fragrances, were evaluated to determine their repellency against the house fly *Musca domestica*. The fragrances were applied to the point of saturation on two inch by three inch fragrance blotters. After the blotters were treated they were placed in sealed plastic bags and transported to the field. In the field they were positioned at twenty foot intervals along the outside walls of two high-rise open-sided caged layer poultry houses having high numbers of adult house flies within. Control blotters, which were not treated were also placed in the poultry houses. The blotters were hung with thumb tacks, three feet above the walkway, in a random fashion. The number of house fly fecal specks and visual observations were used to determine the relative repellency of each material.
Results FIG. 1 shows the number of fecal specks which accumulated on each blotter over the duration of a one week trial. As indicated by the Figure, each fragrance blotter and each fragrance combined with a low vapor pressure insect repellant blotter, repelled flies significantly better than the control blotter. Table 2 below shows the various combinations which were used in the study.

TABLE 2

| Sample Number | Composition |
|---|---|
| 20 | Fragrance only |
| 21 | 20 + 25% DEET |
| 22 | 20 + 50% DEET |
| 23 | 20 + 75% DEET |
| 25 | Duplicate of 22 |
| 26 | DEET only |
| 27 | DMP only |
| 28 | 20 + 50/50 blend DEET/DMP |
| 29 | 20 + 5% DEET |
| 32 | Duplicate of 28 |
| 33 | Triplicate of 22 |
| 41 | Duplicate of 26 |
| 42 | Duplicate of 27 |
| 43 | Duplicate of 29 |
| 44 | Duplicate of 20 |
| 45 | 44 + 25% DEET |
| 46 | 44 + 25% Dibutyl phthalate |
| 47 | 44 + 25% MGK-264 |
| 48 | 50% 44 + 50% DEET |
| 49 | 50% 44 + 50% DBP |
| 50 | 50% 44 + 50% MGK-264 |
| 51 | 20% DEET/20% DBP/60% Aroma chemical |
| 52 | 44 + 5% DEET |
| 53 | Duplicate of 44 |
| 0 | No Treatment |

EXAMPLE 4

This example demonstrates that the low vapor pressure insect repellants are completely soluble with the high vapor pressure fragrances.
Materials And Methods Five samples of combinations of low vapor pressure insect repellants and high vapor pressure fragrances were tested by TGA. The analysis was conducted from a temperature range of 30° C. to 375° C. The chamber used to test the samples were initially purged with nitrogen.
Results FIG. 2 shows the thermograms of the five samples (Samples A1, B1, C3, D1 and E1) that were tested and four controls (Control, Solvent F, Solvent G, Solvent H). The fragrance used in each sample and the Control is a citrus pine. As indicated by FIG. 2, each of the thermograms appears as a smooth curve. The smooth thermograms reflect that the low vapor pressure insect repellants were completely soluble with the high vapor pressure fragrances. The thermograms also demonstrate that the fragrance carries a significant concentration of the low vapor pressure insect repellant. Thus, the combinations provide the benefits of both a contact repellant and an area repellant simultaneously. Table 3 below shows the various samples and solvents used in the study.

TABLE 3

| Sample Number | Composition (w/w %) |
|---|---|
| A1 | 80% Fragrance + 20% DBP |
| B1 | 80% Fragrance + 20% DMP |
| C3 | 80% Fragrance + 20% DEET |
| D1 | 80% Fragrance + 10% DBP + 10% DMP |
| E1 | 70% Fragrance + 10% DBP + 10% DMP + 10% DEET |
| Solvent F | 100% DBP |
| Solvent G | 100% DMP |
| Solvent H | 100% DEET |
| Control | 100% Fragrance |

Now that the preferred embodiments of the invention have been described in detail, various modifications and improvements thereon will become readily apparent to those skilled in the art. Accordingly, the spirit and scope of the present invention are to be limited only by the appended claims and not by the following specification.

What is claimed is:

1. An insect repellant composition comprising a high vapor pressure compound and a low vapor pressure insect repellant, wherein the low vapor pressure insect repellant is soluble in the high vapor pressure compound.

2. The composition of claim 1, wherein the high vapor pressure compound comprises a fragrance.

3. The composition of claim 2, wherein the low vapor pressure insect repellant is selected from the group consisting of DEET, DBP, and DMP, alone or in any combination.

4. The composition of claim 1, wherein the low vapor pressure insect repellant comprises DEET.

5. The composition of claim 4, wherein the high vapor pressure compound comprises a fragrance.

6. The composition of claim 5, wherein the fragrance is selected from the group consisting of salicylates, benzoates, lemon oil, orange oil, citronella oil, geraniol, terpineol, garlic oil, grapefruit oil, mints, southernwood, and tea tree oil, alone or in any combination.

7. The composition of claim 5, wherein the DEET comprises about 1% to about 80% by weight of the composition.

8. The composition of claim 7, wherein the DEET comprises about 1% to about 50% by weight of the composition.

9. The composition of claim 8, wherein the DEET comprises about 1% to about 5% by weight of the composition.

10. The composition of claim 1, wherein the high vapor pressure compound and the low vapor pressure insect repellant are present in sufficient quantities and concentrations to effectively repel insects.

11. The composition of claim 1, wherein said composition is effective both as a contact repellant and as an area repellent.

12. The composition of claim 1, wherein said composition is effective in repelling insects selected from the group consisting of flies, mosquitoes, yellow jackets and ants.

13. An insect repellent composition comprising a high vapor pressure compound, a low vapor pressure insect repellent, and an absorption substrate carrier, wherein the low vapor pressure insect repellent is soluble in the high vapor pressure compound.

14. The composition of claim 13, wherein the high vapor pressure compound comprises a fragrance.

15. The composition of claim 14, wherein the low vapor pressure insect repellent is selected from the group consisting of DEET, DBP, and DMP, alone or in any combination.

16. The composition of claim 13, wherein the low vapor pressure insect repellent comprises DEET.

17. The composition of claim 16, wherein the high vapor pressure compound comprises a fragrance.

18. The composition of claim 17, wherein the fragrance is selected from the group consisting of salicylates, benzoates, lemon oil, orange oil, citronella oil, geraniol, terpineol, garlic oil, grapefruit oil, mints, southernwood, and tea tree oil, alone or in any combination.

19. The composition of claim 13, wherein the absorption substrate carrier is selected from the group consisting of paper, plastisol, gel, fabric, clay, wax, and plastic.

20. The composition of claim 17, wherein the DEBT comprises up to about 80% by weight of the composition.

21. The composition of claim 20, wherein the DEET comprises up to about 50% by weight of the composition.

22. The composition of claim 21, wherein the DEET comprises up to about 5% by weight of the composition.

23. The composition of claim 13, wherein the high vapor pressure compound and the low vapor pressure insect repellant are present in sufficient quantities and concentrations to effectively repel insects.

24. The composition of claim 13, wherein said composition is effective both as a contact repellant and as an area repellant.

25. The composition of claim 13, wherein said composition is effective in repelling insects selected from the group consisting of flies, mosquitoes, yellow jackets and ants.

26. A method of repelling insects from an area, comprising exposing the area to the composition of any one of claims 1–25.

* * * * *